United States Patent [19]

Otten

[11] Patent Number: 4,672,971
[45] Date of Patent: Jun. 16, 1987

[54] OXYGEN SENSOR

[75] Inventor: Josephus M. Otten, Miami, Fla.

[73] Assignee: Sentron v.o.f., Roden, Netherlands

[21] Appl. No.: 745,271

[22] Filed: Jun. 14, 1985

[30] Foreign Application Priority Data

Jun. 21, 1984 [NL] Netherlands .................... 8401966

[51] Int. Cl.$^4$ ............................................. A61B 5/00
[52] U.S. Cl. .................................... 128/635; 204/403; 204/415; 204/431
[58] Field of Search ............... 128/635; 204/403, 414, 204/415, 431, 432

[56] References Cited

U.S. PATENT DOCUMENTS

| | | | |
|---|---|---|---|
| 3,259,124 | 7/1966 | Hillier et al. | 128/635 |
| 3,314,864 | 4/1967 | Hensch | 204/431 X |
| 4,183,791 | 1/1980 | Schick et al. | 204/56.1 |
| 4,268,370 | 5/1981 | Neti | 204/415 |
| 4,445,999 | 5/1984 | Baxter | 204/414 |

FOREIGN PATENT DOCUMENTS 2605568 8/1976 Fed. Rep. of Germany ...... 204/415
2624266 12/1977 Fed. Rep. of Germany .

OTHER PUBLICATIONS

Fatt, *Polarographic Oxygen Sensor*, CRC Press, Inc., 1976, pp. 13-27.

*Primary Examiner*—Lee S. Cohen
*Attorney, Agent, or Firm*—Lockwood, Alex, Fitzggibon & Cummings

[57] ABSTRACT

An oxygen sensor and method of monitoring the oxygen content of blood or other body fluids are provided, which oxygen sensor and method achieve monitoring of enhanced accuracy that is not substantially effected by the presence of an anaesthetic within the fluid being monitored. The electrolyte used in connection with this invention includes a preferential adsorption component that exhibits adsorption to the cathode of the sensor which is in preference to adsorption of the anaesthetic to the cathode of the sensor.

10 Claims, 4 Drawing Figures

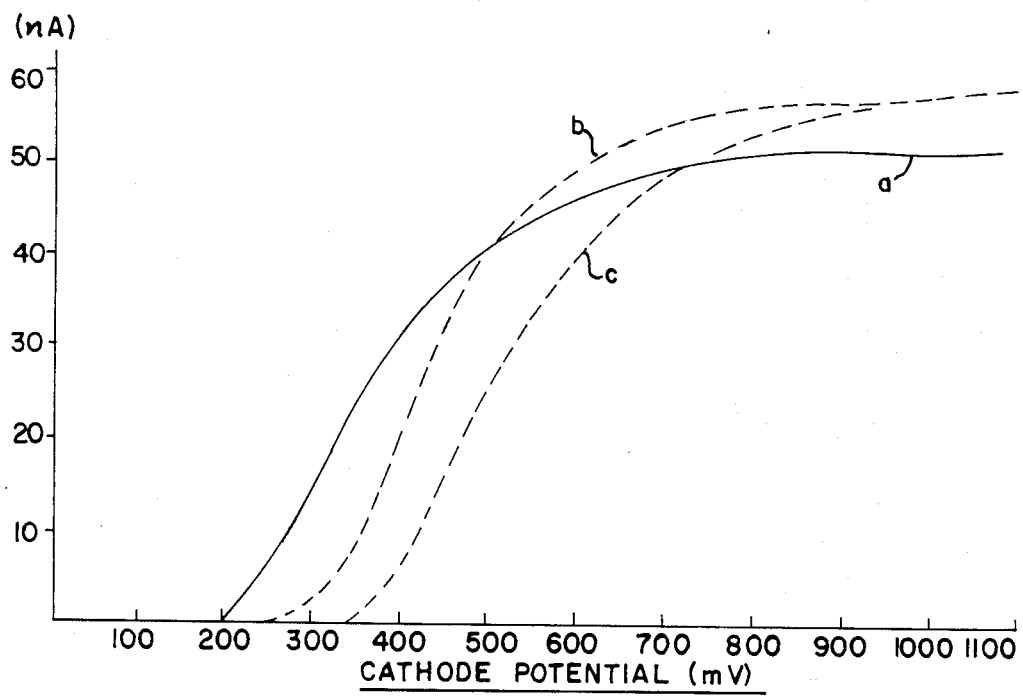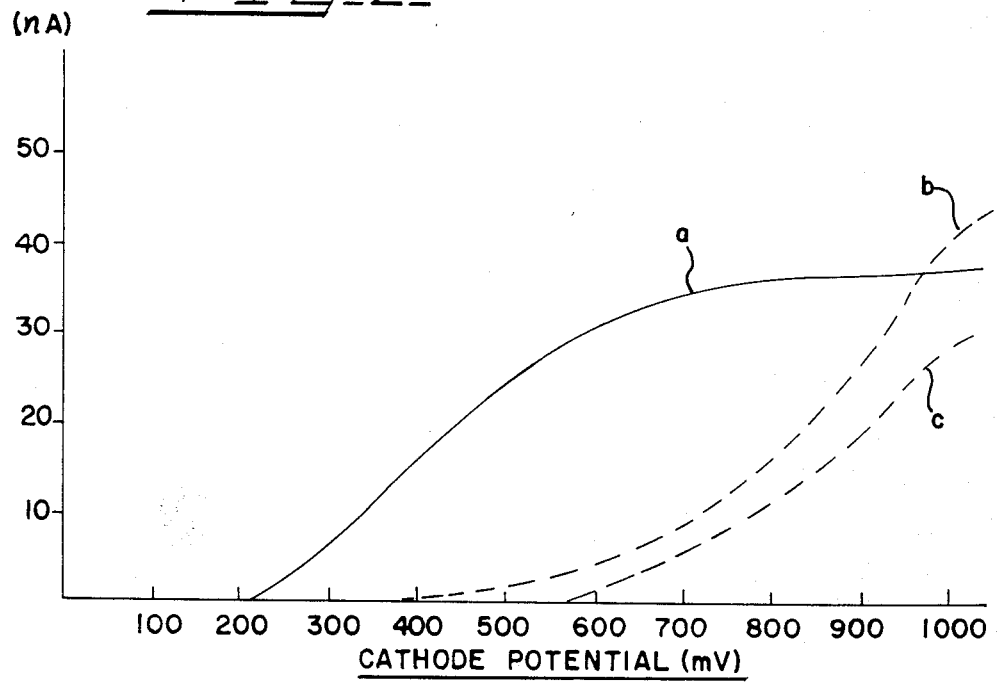

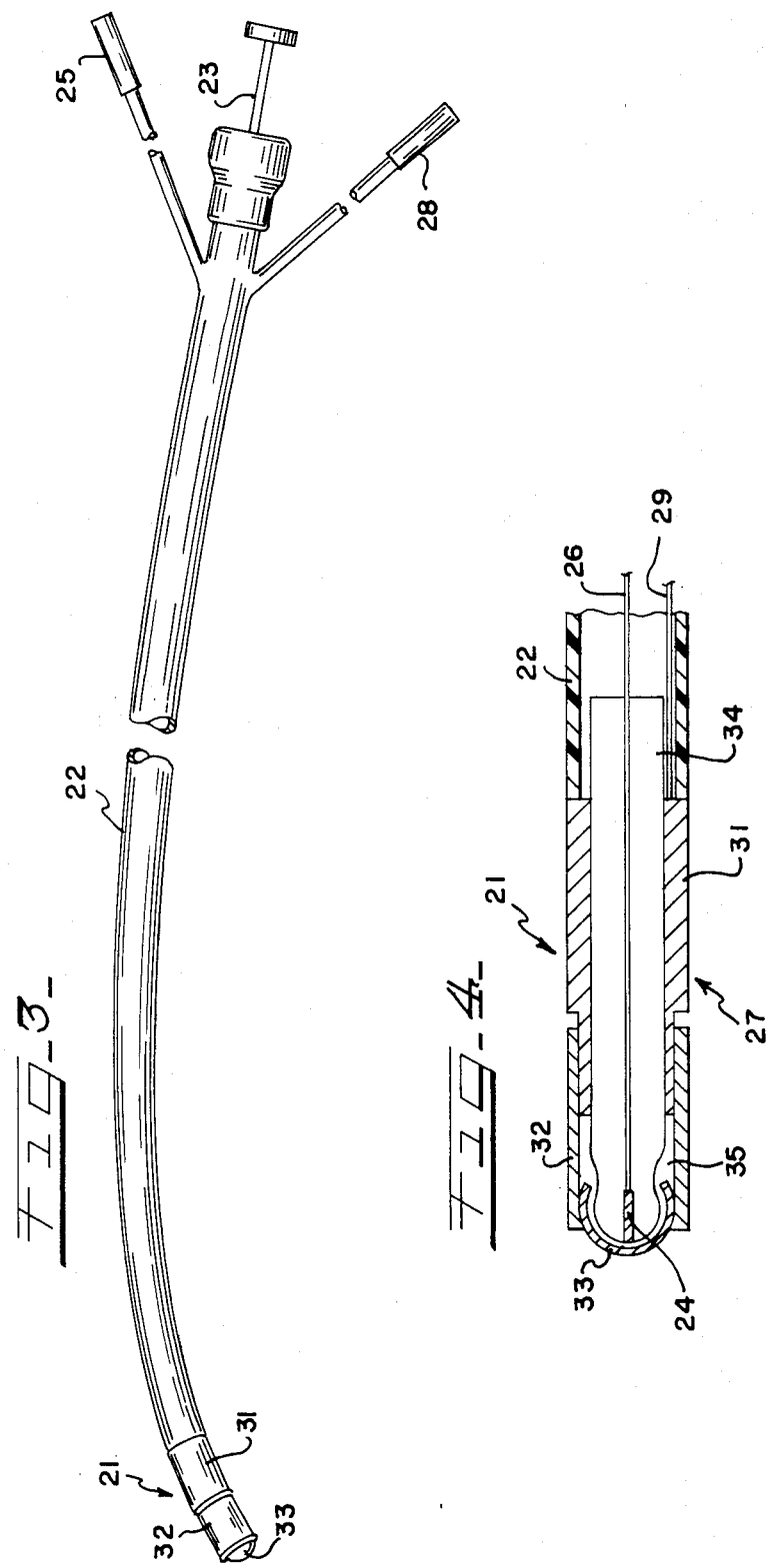

OXYGEN SENSOR

BACKGROUND AND DESCRIPTION OF THE INVENTION

The present invention generally relates to an oxygen sensor that is of the membrane-covered bipolar type, more particularly an oxygen sensor that is suitable for in vivo as well as in vitro measurement of the pO₂ of blood or other body fluids when administering an anaesthetic and to the method of using same. Sensors of this invention are particularly useful when they are designed so as to be incorporated within a catheter whereby the portion of the device for contacting the fluid to be measured may be maneuvered to a desired location within the body of the patient to whom an anaesthetic had been administered. The oxygen sensor is capable of measuring the oxygen content at such a location in a manner that achieves enhanced accuracy by substantially eliminating the interference effects of the anaesthetic with the oxygen measurement mechanism.

Membrane-covered bipolar oxygen sensors, which are generally known as sensors of the Clark cell type, are known to be suitable for the determination of the oxygen content of blood and the like, including in vivo applications by which the cell is inserted into the patient by means of a catheter. Determining the oxygen content of blood or other body fluids is of great importance when, for example, monitoring the condition of a patient who is being treated while being anaesthesized. If the anaesthetic used in this regard is one of the common inhalation anaesthetics such as Halothane (2-bromo-2-chloro-1,1,1-trifluoroethane), Enflurane (2-chloro-1-difluoromethoxy-1,1,2-trifluoroethane), nitrous oxide and the like, such anaesthetics enter the blood stream of the patient and almost inevitably find their way to the location at which the oxygen concentration is being measured by the device, which creates a problem since these anaesthetics typically affect the determination of the oxygen content of the fluid. Oxygen is reduced at the cathode of a Clark-cell type of sensor, and this problem arises primarily because anaesthetics such as Halothane are likewise reduced at the cathode of a Clark-cell type of sensor, the problem being particularly difficult since the electrode potential range of electroreduction of anaesthetics such as Halothane overlaps the electrode potential range of electroreduction of oxygen.

As a result, the current that is measured at a fixed electrode potential by a Clark-cell type of sensor is not defined umambiguously, but the current measured at that fixed electrode potential is the sum of the currents generated by the reduction of oxygen and by the reduction of Halothane or the like. Moreover, this measurement of the oxygen content is further adversely affected by the fact that, due to the low rate of diffusion of anaesthetics such as Halothane through a membrane-covered bipolar oxygen sensor of the Clark cell type, a trailing effect occurs in the sense that a Halothane reduction current is still being measured long after the administration of Halothane to the patient has been terminated.

The present invention substantially eliminates or significantly decreases this type of interference with oxygen concentration measurement that is encountered by a membrane-covered bipolar oxygen sensor, which interference is generated by the presence of an anaesthetic within the body fluid being monitored. This decrease in interference is accomplished primarily by utilizing a cell electrolyte composition that includes a component which exhibits adsorption to the cathode in preference to adsorption of the anaesthetic to the cathode. The invention is based primarily upon the discovery that, for anaesthetics such as Halothane, the first stage in their electroreduction process concerns the adsorption thereof to the cathode surface of a membrane-covered bipolar oxygen sensor of the Clark cell type. This is illustrated by the following reaction equations:

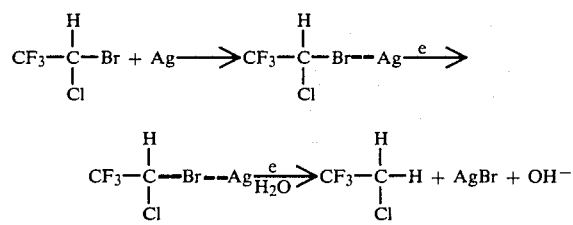

The adsorption illustrated above is substantially prevented in accordance with the present invention. It is suprising that a solution to this problem of anaesthetic interference with oxygen concentration measurement is solved by including a substance within the electrolyte that adsorbs to the cathode and in preference to this adsorption of an anaesthetic such as Halothane to the cathode surface. This preferential adsorption of the electrolyte component results in a change in the properties of the cathode surface, which change typically has an effect only on the activity of the anaesthetic but does not have a substantial effect on the oxygen-reduction process.

It is accordingly a general object of this invention to provide an improved membrane-covered bipolar oxygen sensor of the Clark-cell type.

Another object of the present invention is to provide an improved membrane-covered bipolar oxygen sensor and method of its use that completely or substantially eliminate adverse effects on the measurement of the oxygen content within a body fluid that are caused by the occurrence of a cathodic reduction that fully or partially coincides with that of oxygen.

Another object of the present invention is to provide an improved membrane-covered bipolar oxygen sensor and method which rely upon the adsorption of an electrolyte component to the cathode, which component adsorption is in preference to that of an anaesthetic that may be present within the fluid being measured.

Another object of this invention is to provide an improved membrane-covered bipolar oxygen sensor and method that substantially prevent the reduction of an anaesthetic such as Halothane at the electrode surface while avoiding an significant effect on the reduction of oxygen at the electrode surface.

Another object of the present invention is to provide an improved membrane-covered bipolar oxygen sensor and method that exploit the discovery that the adsorption of an anaesthetic such as Halothane is the first step in the electroreduction process of the anaesthetic.

Another object of the present invention is to provide an improved membrane-covered bipolar oxygen sensor and method that exhibit preventive adsorption of an electrolyte component to its cathode in order to change the properties of the cathode surface without significantly affecting the oxygen reduction process.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 provides a plot of cathode potential versus current strength for a membrane-covered bipolar oxygen sensor of the Clark cell type that is not in accordance with the present invention;

FIG. 2 provides a plot of cathode potential versus current strength for a membrane-covered bipolar oxygen sensor of the Clark cell type that is in accordance with the present invention;

FIG. 3 is an elevational view of a typical catheter structure suitable for incorporating the membrane-covered bipolar oxygen sensor Clark-cell assembly in accordance with this invention; and FIG. 4 is a sectional view generally along the line 4—4 of FIG. 3.

DESCRIPTION OF THE PARTICULAR EMBODIMENTS

Referring to FIG. 3 and FIG. 4, these drawings generally depict, by reference numeral 21, a membrane-covered bipolar oxygen sensor of the Clark cell type, such sensor cell 21 being mounted at the distal end portion of a catheter 22, which may be maneuverable by means of a stylet 23 in accordance with generally known procedures.

With more particular reference to the bipolar oxygen sensor cell 21, such includes a cathode 24 which is in electrical communication with a terminal assembly 25 through an electrical conductor 26. An anode assembly, generally designated as 27, is in electrical communication with another terminal assembly 28 through an electrical conductor 29. The illustrated anode assembly 27 includes a tube portion 31 and a cap portion 32. A membrane 33 seals the distal end of the bipolar oxygen sensor cell 21. Membrane 33 is oxygen-permeable and is made of a material such as Copel, which is a mixture of silicone rubber and a polycarbonate. An enclosure 34 is provided, and an electrolyte 35 contacts both the cathode 24 and the anode assembly 27. The oxygen-permeable membrane 33 contacts the fluid to be measured when the device is in use.

With more particular reference to the electrolyte 35, such is of a composition generally suitable for its intended use, typically including organic and/or inorganic compounds that are non-toxic and are suitable and safe for biomedical uses, including those that are acceptable for conducting in vivo measurements of the oxygen contents of blood. Electrolyte 35 also contains a preferential adsorption component that is adsorbed to the cathode 24 in preference to adsorption to the cathode 24 of an anaesthetic such as Halothane, which preferential adsorption component does not substantially affect the electroreduction process that occurs with respect to oxygen within the fluid being monitored.

Preferred preferential adsorption components are inorganic salts, especially metal halides such as lithium chloride, sodium iodide, potassium iodide, and the like. Sodium iodide or potassium iodide are preferred. The concentration of the preferential adsorption component in the electrolyte 35 is one that is sufficient to substantially prevent adsorption in the electrolyte 35 of the particular anaesthetic administered to the patient or present in the fluid being monitored. Generally, the concentration of such preferential adsorption component is on the order of about 0.01M to about 0.0001M, based on the total volume of the electrolyte 35.

The advantages of, and the results achieved by, the membrane-covered bipolar oxygen sensor 21 in accordance with this invention are illustrated by the data reported in FIG. 1 and in FIG. 2. These diagrams illustrate results of reduction at the silver cathode of a membrane-covered bipolar oxygen sensor such as that generally illustrated in FIG. 4. Such measurement is corrected for zero current, which is the current strength when nitrogen is passed through, and the data of the diagrams are recorded at a recording rate of 1 mV/second. In both FIG. 1 and FIG. 2, the current strength in nA is plotted on the Y-axis, and the cathode potential in mV relative to a silver/silver chloride reference electrode is plotted on the X-axis. In both FIG. 1 and FIG. 2, each curve plots such respective current strengths and cathode potentials as they are measured for different fluids monitored by the respective oxygen sensors. In both FIG. 1 and FIG. 2, each of the "a" curves reports data generated when the medium being measured was air, each "b" curve reports data generated when the medium measured was a mixture of 2% Halothane in nitrogen, and each of the "c" curves reports data generated when the medium measured was a mixture of 2% Halothane in air.

The data reported in FIG. 1 were generated by monitoring these three different fluids with a membrane-covered bipolar oxygen sensor that is not in accordance with this invention in that the electrolyte did not include a preferential adsorption component as described herein, although it did contain a bicarbonate and sodium chloride. Data reported in FIG. 2 were generated in substantially the same manner as the FIG. 1 data and by means of a membrane-covered bipolar oxygen sensor substantially identical with that used in connection with FIG. 1, except the FIG. 2 data were generated with a sensor in accordance with this invention and which contained $10^{-3}$M potassium iodide as the preferential adsorption component of the electrolyte 35, which also included a bicarbonate and sodium chloride.

A comparison of the curves of FIG. 1 with the curves of FIG. 2 graphically illustrates the effect of the preferential adsorption component upon the electroreduction potential of the monitored fluids that included Halothane. Each of curves "b" and "c" in FIG. 2 show an apparent shift in the reduction potential of Halothane of about 250 to 300 mV in the direction of higher cathodic values when compared with respective curves "b" and "c" of FIG. 1. Additionally, the FIG. 2 curves "b" and "c" appear to be less steep than the corresponding curves "b" and "c" of FIG. 1. While curve "a" of FIG. 2 shows a curve that is less steep than curve "a" of FIG. 1, the reduction commences at substantially the same cathodic potential, which indicates that the reduction reaction for the monitored fluid which is primarily oxygen is effected to a much lesser degree than for a monitored fluid that contains an anaesthetic such as Halothane. This indicates that, while the present invention exhibits preferential adsorption with respect to anaesthetics such as Halothane, the invention does not greatly affect the cathodic values of oxygen, which is the material that the membrane-covered bipolar sensor according to this invention is designed to monitor.

It will be understood that the embodiments of the present invention which have been described are illustrative of some of the applications of the principles of the present invention. Numerous modifications may be made by those skilled in the art without departing from the true spirit and scope of the invention.

I claim:

1. A membrane-covered bipolar oxygen sensor for measurement of the concentration of oxygen in blood or other body fluids to be monitored, comprising:
    an enclosure assembly containing an electrolyte and having an open end for contacting the fluid to be monitored;
    an oxygen-permeable membrane that seals said open end of the enclosure assembly;
    a cathode and an anode in contact with said electrolyte; and
    said electrolyte includes a preferential cathode adsorption component that absorbs to the cathode in preference to adsorption to the cathode of an anaesthetic included within the fluid to be monitored, said preferential cathode adsorption component being present in said electrolyte at a concentration that is sufficient to substantially prevent adsorption of the anaesthetic to said cathode, said preferential cathode adsorption component being an inorganic salt having an iodide ion or a lithium ion.

2. The oxygen sensor according to claim 1, wherein said preferential cathode adsorption component of the electrolyte is a metal iodide.

3. The oxygen sensor according to claim 2, wherein said metal iodide is selected from the group consisting of potassium iodide and sodium iodide.

4. The oxygen sensor according to claim 1, wherein said inorganic salt is lithium chloride.

5. The oxygen sensor according to claim 1, wherein said enclosure assembly includes a catheter having a proximal end and a distal end, and wherein said open end and said membrane are positioned at said distal end of the catheter.

6. The oxygen sensor according to claim 1, wherein said cathode is generally surrounded by said anode, and wherein said anode is generally symmetrical.

7. The oxygen sensor according to claim 1, wherein said concentration of the preferential adsorption component is on the order of about 0.01M to about 0.0001M of the electrolyte.

8. A method for measuring the oxygen content of blood and other body fluids being monitored when administering an anaesthetic, comprising:
    providing a membrane-covered bipolar oxygen sensor having an enclosure assembly containing an electrolyte, an open end for contacting the fluid being monitored, an oxygen-permeable membrane sealing the open end, and a cathode and an anode in contact with the electrolyte;
    adding to said electrolyte a preferential cathode adsorption component that exhibits adsorption to the cathode in preference to adsorption of an anaesthetic to the cathode said preferential cathode adsorption component being an inorganic salt having an iodide ion or a lithium ion; and
    contacting the open end of the oxygen sensor with the fluid to be monitored, said fluid including an anaesthetic.

9. The method according to claim 8, wherein said preferential cathode adsorption component is selected from the group consisting of potassium iodide, sodium iodide and lithium chloride.

10. The method according to claim 8, further including substantially eliminating interference effects of the anaesthetic upon oxygen concentration measurement while substantially avoiding effecting of the electroreduction of oxygen.

* * * * *

UNITED STATES PATENT AND TRADEMARK OFFICE
CERTIFICATE OF CORRECTION

PATENT NO. : 4,672,971

DATED : June 16, 1987

INVENTOR(S) : Josephus M. Otten

It is certified that error appears in the above-identified patent and that said Letters Patent is hereby corrected as shown below:

Column 1, line 50, "umambiguously" should read --unambiguously--.
Column 2, line 55, "an" should read --any--.
Column 5, line 17, "absorbs" should read --adsorbs--.

Signed and Sealed this

Nineteenth Day of July, 1988

Attest:

DONALD J. QUIGG

Attesting Officer

Commissioner of Patents and Trademarks